(12) United States Patent
Nhan et al.

(10) Patent No.: US 10,105,507 B2
(45) Date of Patent: Oct. 23, 2018

(54) DEVICE FOR PROVIDING AN AUXILIARY AIR PASSAGE TO THE TRACHEA

(71) Applicants: Carol Nhan, Montreal (CA); Rafal Bielecki, Montreal (CA)

(72) Inventors: Carol Nhan, Montreal (CA); Rafal Bielecki, Montreal (CA)

( * ) Notice: Subject to any disclaimer, the term of this patent is extended or adjusted under 35 U.S.C. 154(b) by 605 days.

(21) Appl. No.: 14/659,185

(22) Filed: Mar. 16, 2015

(65) Prior Publication Data
US 2015/0258294 A1 Sep. 17, 2015

Related U.S. Application Data

(60) Provisional application No. 61/953,241, filed on Mar. 14, 2014.

(51) Int. Cl.
*A61M 16/04* (2006.01)
*A61M 16/00* (2006.01)

(52) U.S. Cl.
CPC .............................. *A61M 16/0472* (2013.01)

(58) Field of Classification Search
CPC .. A61M 16/00; A61M 16/04; A61M 16/0402; A61M 16/0406; A61M 16/0463; A61M 16/047; A61M 16/0475; A61M 16/0488; A61M 16/0816; A61M 16/0465; A61M 16/0472; A61M 2210/1032; A61M 25/00; A61M 25/0014; A61M 25/0045; A61M 25/0069; A61M 25/007; A61M 25/06; A61M 25/0612; A61M 2025/0008;
(Continued)

(56) References Cited

U.S. PATENT DOCUMENTS 3,307,551 A * 3/1967 Violet, Jr. .......... A61M 16/0472
128/207.29
3,817,250 A * 6/1974 Weiss ................ A61M 16/0472
128/207.29
(Continued)

FOREIGN PATENT DOCUMENTS

DE 10210215 A1 * 9/2003 ........ A61M 16/0472
WO WO 2014018565 A1 * 1/2014 ........ A61M 25/0041

OTHER PUBLICATIONS

Machine translation of DE 10210215 A1.*

*Primary Examiner* — Jackie Tan-Uyen T Ho
*Assistant Examiner* — Joseph D Boecker
(74) *Attorney, Agent, or Firm* — Benoit & Cote Inc.; Michel Sofia

(57) ABSTRACT

A device for providing an auxiliary aft passage to a trachea comprises a cannula member, a trocar member and a cap member. The cannula member has longitudinal walls defining a channel, proximal and distal openings at opposed ends of the channel, and a side opening near a distal end of the longitudinal walls. The trocar member includes a proximal flanged end and an elongated member extending from the flanged end, the elongated member being insertable within the channel and having a pointed end projecting through the distal opening when the elongated member is inserted in the channel. The cap member has an inner cavity and is adapted to sealingly engage the cannula member, when the device is not in use, such that the longitudinal walls of the cannula member are contained within the inner cavity and the sharp tip of the trocar member is protectively housed within the cap member.

30 Claims, 3 Drawing Sheets

(58) Field of Classification Search
CPC . A61B 17/34; A61B 17/3415; A61B 17/3417;
A61B 17/3421; A61B 17/3474
USPC ............... 128/200.26, 207.14, 207.29, 912;
600/529; 604/164.01, 171, 264, 533;
606/185
See application file for complete search history.

(56) References Cited

U.S. PATENT DOCUMENTS

| | | | | |
|---|---|---|---|---|
| 4,291,690 | A * | 9/1981 | Jessen | A61M 16/0472 |
| | | | | 128/200.26 |
| 4,520,810 | A * | 6/1985 | Weiss | A61B 17/3415 |
| | | | | 128/200.26 |
| 4,556,059 | A * | 12/1985 | Adamson, Jr. | A61M 16/0472 |
| | | | | 128/207.14 |
| 4,869,718 | A * | 9/1989 | Brader | A61M 16/0465 |
| | | | | 128/207.17 |
| 5,522,831 | A * | 6/1996 | Sleister | A61B 17/3417 |
| | | | | 600/564 |
| 5,546,339 | A | 8/1996 | Oyama | |
| 5,546,939 | A * | 8/1996 | French | A61M 16/0472 |
| | | | | 128/200.26 |
| 6,330,882 | B1 * | 12/2001 | French | A61M 16/0472 |
| | | | | 128/200.26 |
| 2002/0193806 | A1 * | 12/2002 | Moenning | A61B 17/3417 |
| | | | | 606/108 |
| 2009/0157085 | A1 * | 6/2009 | Melsheimer | A61B 17/8811 |
| | | | | 606/93 |
| 2015/0182716 | A1 * | 7/2015 | Wolf | A61M 16/04 |
| | | | | 600/245 |

* cited by examiner

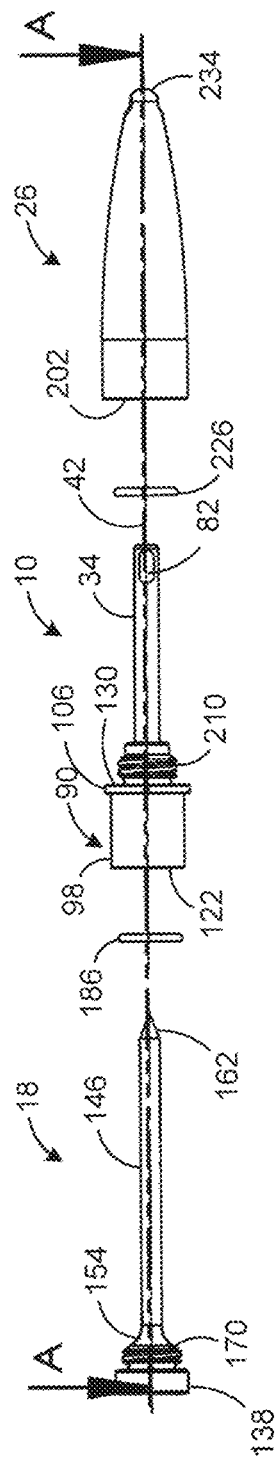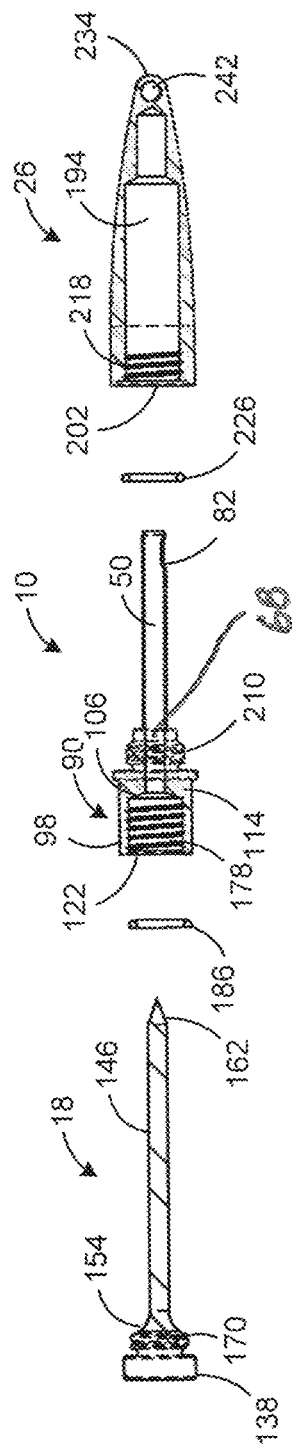

DEVICE FOR PROVIDING AN AUXILIARY AIR PASSAGE TO THE TRACHEA

CROSS REFERENCE TO RELATED APPLICATIONS

This application claims priority on U.S. Provisional Application No. 61/953,241, filed on Mar. 14, 2014, which is herein incorporated by reference.

FIELD

The present subject-matter relates to a device for providing an urgent auxiliary air passage to the trachea, for example, to be used in a tracheotomy, or cricothyrotomy.

INTRODUCTION

Where a patient cannot be ventilated and be cannot intubated, for example due to obstruction of the airway of the patient, providing an auxiliary air passage to the trachea allows the patient to continue receiving air and can be lifesaving.

U.S. Pat. No. 5,546,939 issued on Aug. 20, 1996 to French discloses an apparatus for performing emergency tracheostomies, by inserting the apparatus into the trachea of a patient, the apparatus including an air delivery tube, having a body portion, a first upper threaded end, a second lower end, and a bore extending throughout the body portion to accommodate air flow through the air delivery tube. The apparatus also includes a trocar member having a body portion insertable through the bore of the air delivery tube, with a pointed end partially protruding out of the second lower end of the tube for piercing the tracheal wall during insertion of a portion of the air delivery tube into the trachea. The apparatus further includes an extendor portion engageable to the first upper end of the air delivery tube after the tube has been inserted into the trachea, and the trocar member has been removed from the air delivery tube, for providing a point of delivering air flow through the air delivery tube into the trachea of a patient above the tracheal wall. The air delivery tube and the trocar member are insertable in the extendor member and sealed therein when not in use.

SUMMARY

Therefore, the embodiments described herein provide in one aspect a device for providing an auxiliary air passage to a trachea, the device comprising: a cannula member having a longitudinal wall defining a channel, first and second openings transverse to a longitudinal axis of the channel and a third opening defined on a side of the longitudinal wall; a trocar member having a flanged end and an elongated member extending from the flanged end, the elongated member being insertable within the channel, a pointed end of the elongated member projecting through the first opening when the elongated member is inserted in the channel; a cap member for sealingly engaging at least one of the cannula member and the trocar member and defining an inner cavity, a portion of the cannula member being sealed within the inner cavity when the cap member sealingly engages said at least one of the cannula member and the trocar member.

The embodiments described herein provide in another aspect a device for providing an auxiliary air passage to a trachea, the device comprising: a cannula member having an adapter portion and a longitudinal wall extending longitudinally from an annular base of the adapter portion, the adapter portion having a circumferential wall defining with the annular base an adapter chamber, the longitudinal wall defining a channel and an end opening, the channel being in communication with the adapter chamber via an opening in the annular base; a trocar member having a flanged end and an elongated member extending from the flanged end, the flanged end being sealingly securable with the cannula member to seal the adapter chamber and the elongated member being insertable within the channel, a pointed end of the elongated member projecting through the end opening when the elongated member is inserted in the cannula member; a cap member for sealingly engaging at least one of the cannula member and the trocar member and defining an inner cavity, a portion of the cannula member being sealed within the inner cavity when the cap member sealingly engages said at least one of the cannula member and the trocar member.

The embodiments described herein provide in a further aspect a method for providing an auxiliary air passage in a trachea, the method comprising: disengaging a cap member from a trocar member and a cannula member to expose a pointed end of the trocar member; piercing with the trocar member a neck region and a cricothyroid membrane or an anterior wall of the trachea to position a side opening of the cannula member within the trachea; and disengaging the trocar member from the cannula member to expose an opening in the cannula member, which is in fluid communication with the side opening.

The embodiments described herein provide in a still further aspect a device for providing an auxiliary air passage to a trachea, the device comprising: a cannula having opposed distal and proximal openings and a channel therebetween, a third opening being defined on a side of the cannula at a distal end thereof; and a trocar having an elongated member insertable within the channel, a penetrating end of the elongated member projecting through the distal opening when the elongated member is inserted in the cannula, and being adapted for penetrating a patient and for positioning the distal end of the cannula in a trachea of the patient.

The embodiments described herein provide in a still further aspect a device for providing an auxiliary air passage to a trachea, the device comprising: a cannula having distal and proximal openings and a channel therebetween, the cannula having a proximal adapter in communication with the channel; a trocar having an elongated member insertable within the channel, the elongated member having a penetrating end, the elongated member projecting through the distal opening of the cannula when the elongated member is inserted in the cannula and the cannula is attached to the trocar in an assembled position thereof, the trocar and the cannula being adapted in the assembled position to penetrate a patient such as to position the distal end of the cannula in a trachea of the patient.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which:

FIG. 3 is an exploded side view of the device of FIG. 1; and

FIG. 4 is a cross-sectional exploded view of the device taken along the line A-A of FIG. 3.

DESCRIPTION OF VARIOUS EMBODIMENTS

Figure 1:
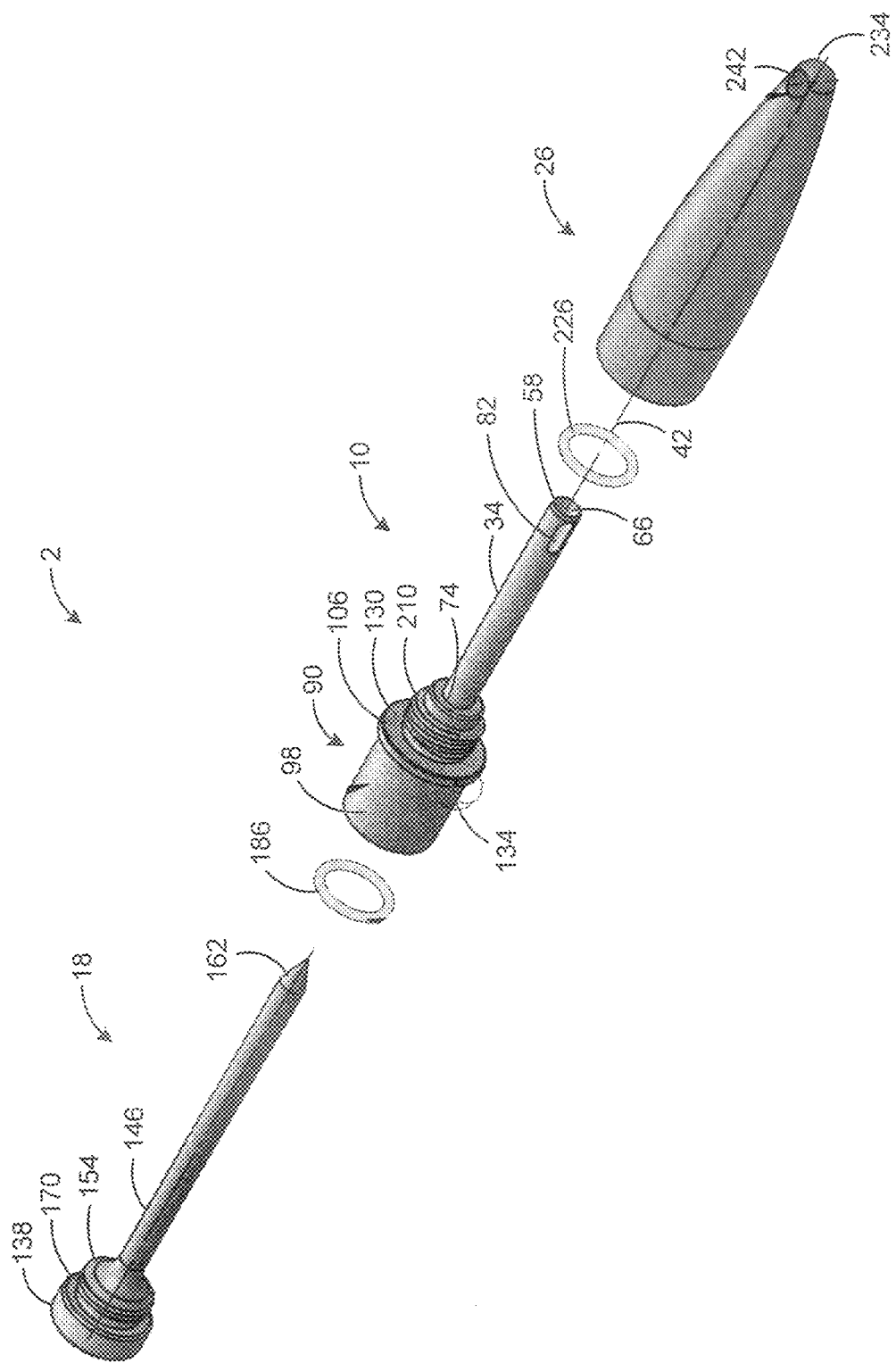
FIG. 1 is an exploded view of a device according to various exemplary embodiments for providing an auxiliary air passage to the trachea.
Figure 2:
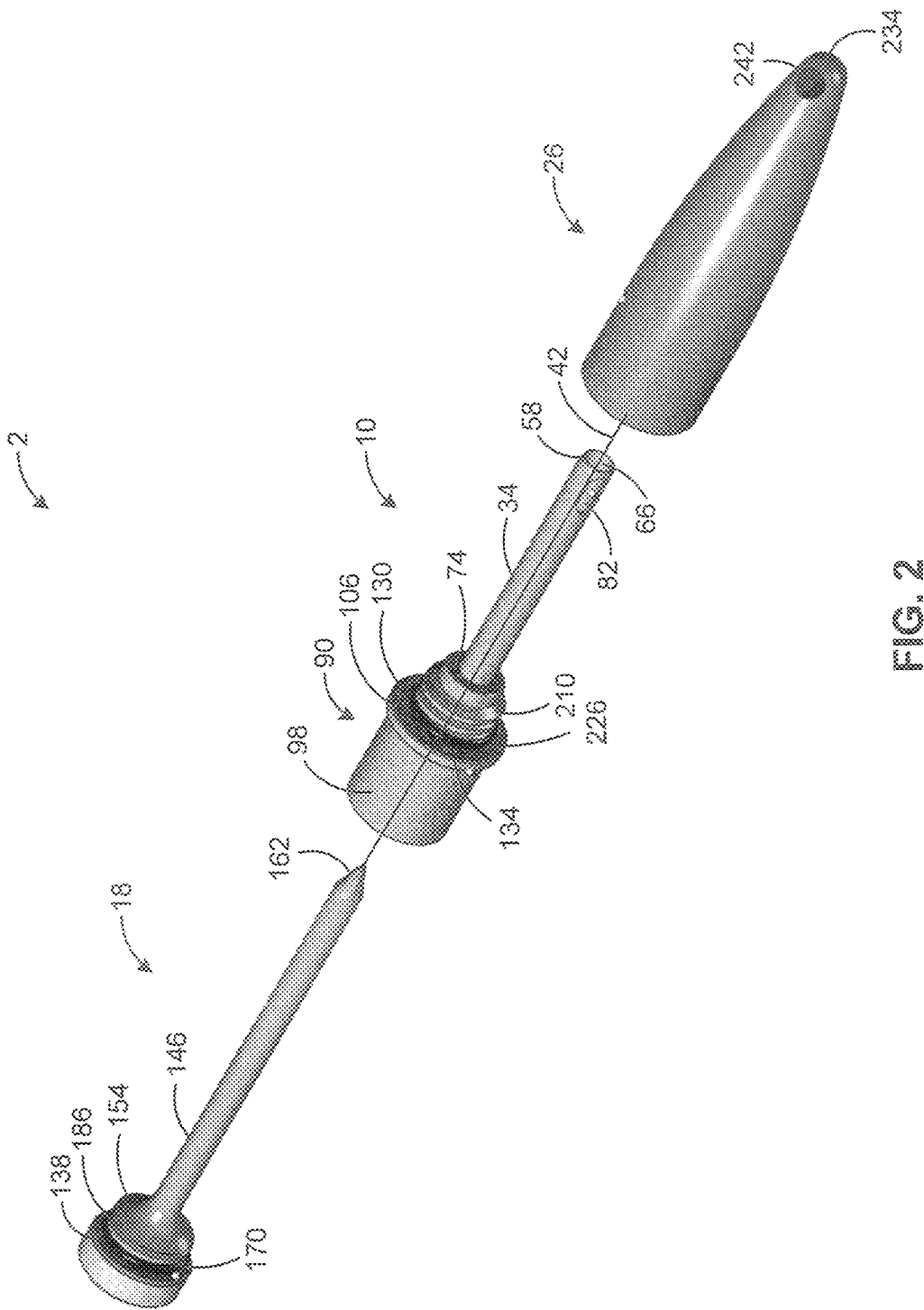
FIG. 2 is another exploded view of the device of FIG. 1.

Referring now to FIGS. 1 to 4, therein illustrated is a portable device 2 according to various exemplary embodiments for providing an auxiliary air passage to the trachea. The device 2 may be used in various procedures for providing an auxiliary air passage to the trachea of a patient to allow the patient to continue receiving air. For example, the device 2 may be used for performing a tracheotomy or cricothyrotomy. The device 2 includes a cannula member 10, a trocar member 18 and a cap member 26. The cannula member 10 and trocar member 18 may be assembled in a first configuration to form a surgical tool for providing the auxiliary air passage to the trachea. The cannula member 10, the trocar member 18 and the cap member 26 may be further assembled together into a second portable configuration. For example, in the second portable configuration, the cannula member 10 and the trocar member 18 may be maintained in a sterilized state with the trocar member 18 being shielded, typically by the cap member 26, to prevent injury.

The cannula member 10 includes a longitudinal wall 34 defining a longitudinal axis 42. An inner surface of the longitudinal wall 34 defines a hollow channel 50 extending in the direction of the longitudinal axis 42. A distal end 58 of the longitudinal wall 34 defines a distal first end opening 66 that is in fluid communication with the channel 50, For example, a plane defining the distal end opening 66 is oriented transversely to the longitudinal axis 42. A proximal end 74 of the longitudinal wall 34 defines a proximal second end opening 68 opposite the distal end opening 66. The proximal end opening 68 is in fluid communication with the distal end opening 66 via the hollow channel 50. For example, a plane defining the proximal end opening 68 is oriented transversely to the longitudinal axis 42.

According to various exemplary embodiments, the longitudinal wall 34 further defines a third opening, that is a side opening 82 located at the distal end 58. For example, the side opening 82 is located proximate the distal end opening 66 but spaced apart from the distal end opening 66, as herein illustrated. However, the side opening 82 could also extend to the distal end opening 66, such as to merge therewith. It will be appreciated that the side opening 82 is oriented transversely to an orientation of the distal end opening 66. For example, the side opening 82 can be elongated, as herein shown, and oriented longitudinally along the longitudinal wall 34. For instance, the side opening 82 can be oblong, as herein shown.

The side opening 82 is in fluid communication with the channel 50. The side opening 82 may be in fluid communication with the channel 50 independently of the distal end opening 66. For example, where the distal end opening 66 is blocked, fluid communication of the channel 50 with an environment surrounding the longitudinal wall 34 can be maintained via the side opening 82.

According to various exemplary embodiments, the cannula member 10 further includes an adapter portion 90 having a circumferential wall 98 and an annular base 106. The annular base 106 is oriented transversely to the longitudinal axis 42. The circumferential wall 98 and the annular base 106 define together an adapter chamber 114 having an end opening 122. The annular base 106 provides an interface between the circumferential wall 98 and the longitudinal wall 34. The longitudinal wall 34 extends longitudinally from an outer surface 130 of the annular base 106. The channel 50 of the longitudinal wall 34 is further in fluid communication with the adapter chamber 114 via the proximal end opening 68 and an opening of the annular base 106. Accordingly, the end opening 122 of the adapter chamber 114 is in fluid communication with the distal end opening 66. According to various exemplary embodiments where the cannula member 10 includes the side opening 82, the end opening 122 of the adapter chamber 114 may be further in communication with the side opening 82.

According to various exemplary embodiments, the adapter portion 90 may further include a marking 134 located at an angular position about the longitudinal axis 42 corresponding to an angular position of the side opening 82. In other words, the side opening 82 and the marking 134 are in a same plane that extends radially from the longitudinal axis 42. Alignment of the marking 134 with the side opening 82 allows a user to identify the position of the side opening 82 when the side opening 82 is hidden from view. The user will thus be able, from the position of the marking 134, to evaluate where the side opening 82 opens up, thereby enabling the user to manipulate the cannula member 10 so as to typically orient the side opening 82 inferiorly thus directing air towards the lungs. For example, the marking 134 may be a notch or groove formed on the annular base 106, or indicia printed thereon.

According to various exemplary embodiments and as illustrated in FIGS. 1 to 4, a diameter of the circumferential wall 98 of the adapter portion 90 of the cannula member 10 is substantially greater than a diameter of the longitudinal wall 34. Accordingly, the longitudinal wall 34 is narrower than the adapter portion 90. For example, the dimensions of the circumferential wall 98 correspond to the standard dimensions of a ventilation port of a respiratory apparatus that provides air or oxygen to an external device through the ventilation port. It will be appreciated that in this case, the cannula member 10 is the external device of the respiratory apparatus. For example, the respiratory apparatus is an ambubag. When the ventilation port is attached to the adapter portion 90 of the cannula member 10, the respiratory apparatus is in fluid communication with at least one of the distal end opening 66 and side opening 82. Accordingly, air or oxygen provided by the respiratory apparatus is flowed through the distal end opening 66 and/or side opening 82 to an environment surrounding the longitudinal wall 34 adjacent the distal end 58.

According to various exemplary embodiments, the longitudinal wall 34 and the adapter portion 90 of the cannula member 10 are integrally formed. Accordingly, the cannula member 10 includes both a respiratory channel for a tracheostomy (provided by the channel 50 defined by the longitudinal wall 34) and an adapter for attachment with a ventilation port (provided by the adapter portion 90) within a unitary body.

The trocar member 18 includes a flanged end 138 and an elongated member 146 extending therefrom. For example, a proximal end 154 of the elongated member 146 proximate the flanged end 138 is outwardly tapered. A distal end 162 of the elongated member 146 is pointed. The pointed distal end 162 of the elongated member 146 forms a piercing member operable to pierce the soft tissues of the neck overlying the trachea and the cricothyroid membrane or anterior tracheal wall of a patient in order to enter the airway.

The outer diameter of elongated member 146 is appropriately sized according to an inner diameter of the longitudinal wall 34 of the cannula member 10 so that the elongated member 146 is insertable within the channel 50, The length of the elongated member 146 is further appropriately sized according to a length of the channel 50 so that the pointed end 162 of the elongated member 146 projects through the distal end opening 66 when the elongated member 146 is inserted within the channel 50, For example, the length of the elongated member 146 may be appropriately sized according to a length of the channel 50 and a length of the adapter chamber 114 so that the pointed end 162 of the elongated member 146 projects through the distal end opening 66 when the elongated member 146 is inserted in the cannula member 10.

According to various exemplary embodiments, the trocar member 18 may be sealingly engageable with the cannula member 10 to seal the end opening 122 of the adapter chamber 114. Sealing the end opening 122 of the adapter chamber 114 further seals the proximal end opening 68 of the channel 50. For example, the trocar member 18 includes an externally threaded portion 170 for engaging internal threads 178 of the circumferential wall 98 of the adapter portion 90, thereby securing the trocar member 18 to the cannula member 10. For example, the externally threaded portion 170 may correspond to an outer portion of the flanged end 138 or to an outer portion of the proximal end 154 of the elongated member 146. For example, a first sealing member 186, such as an O-ring, may be further provided about the externally threaded portion 170 to aid in forming a seal.

When the elongated member 146 and at least internal surfaces of the cannula member 10 have been sterilized, sealing the adapter chamber 114 when the elongated member 146 is inserted within the channel 50 maintains the elongated member 146 and at least the internal surfaces of the cannula member 10 in their sterilized states. The outer portion of cannula member 10, which also has been sterilized, will remain in its sterilized state when contained within the cap member 26. In fact, all of the areas of the cannula member 10 and of the trocar member 18, which have been made sterile, will remain sterile as long as contained in the cap member 26, i.e. once the cannula member 10 has been sealingly assembled to the cap member 26.

The sealed engagement of the trocar member 18 and cannula member 10 is formed independently of any engagement of the trocar member 18 or cannula member 10 with the cap member 26. For example, a secured engagement of the trocar member 18 and the cannula member 10 is maintained when the cap member 26 is disengaged from the cannula member 10 and/or from the trocar member 18.

Insertion of the elongated member 146 within the channel 50 of the cannula member 10 so that the pointed end 162 projects from the distal end opening 66 forms a tool for providing an auxiliary air passage to the trachea of a patient. The tool is operated by first perform g a piercing action wherein the pointed end 162 is displaced to pierce the skin of the neck region of a patient and to pierce the cricothyroid membrane or the anterior wall of the trachea of the patient. Accordingly, at least the end 58 of the longitudinal wall 34 of the cannula member 10 proximate the distal end opening 66 is positioned within the trachea of the patient, such that the distal end opening 66 and the side opening 82 are both in the trachea.

Furthermore, the cannula member 10 may be rotated to orient the marking 134, and consequently the side opening 82, in a direction promoting air flow into the trachea. For example, the side opening 82 is oriented towards a lower portion of the trachea, i.e. down towards the lungs. The tool is further operated by disengaging the trocar member 18 from the cannula member 10 while maintaining the end 58 of the longitudinal wall 34 within the trachea. For example, the trocar member 18 is unsecured from the cannula member 10 and the elongated member 146 is withdrawn from the channel 50 and adapter chamber 114. Accordingly, the cannula member 10 provides a fluid path between an exterior of the patient and the trachea thereof via at least the proximal end opening 68, the channel 50 and at least one of the distal end opening 66 and side opening 82.

According to various exemplary embodiments where the side opening 82 is provided, the side opening 82 advantageously provides an alternative fluid path where the distal end opening 66 is blocked. For example, during the piercing action or subsequently, the user may have caused the end 58 of the longitudinal wall 34 to abut against an object in the trachea so as to cause the distal end opening 66 to be blocked. For example, the end 58 may be abutting against the posterior wall of the trachea. In such situations, the fluid path between the exterior of the patient and the trachea is maintained via the side opening 82. Advantageously, the user is not required to constantly ensure an accurate depth of insertion of the longitudinal wall 34 within the trachea, such as constantly ensuring that the distal end opening 66 is not abutting against a wall of the trachea.

Secured engagement of the trocar member 18 and cannula member 10 further assists in operating the tool. For example, when performing the piercing action, a user only needs to manipulate one of the cannula member 10 and the trocar member 18. Due to the secured engagement, the other of the cannula member 10 and the trocar member 18 will follow during the piercing action. Accordingly, the user does not need to position his/her fingers so as to simultaneously manipulate both the cannula member 10 and the trocar member 18 during the piercing action.

According to various exemplary embodiments where the cannula member 10 includes the adapter portion 90, disengaging the trocar member 18 from the cannula member 10 readies the cannula member 10 for attachment to a ventilation port of a respiratory apparatus. For example, further attachment of an adapter onto the cannula member 10 is not required in order to attach a ventilation port of a respiratory apparatus with the cannula member.

The cap member 26 defines an inner cavity 194 having an end opening 202. The cap member 26 is further adapted to sealingly engage either the cannula member 10 or the trocar member 18. When so engaged, at least a portion of the cannula member 10 is sealed within the inner cavity 194 of the cap member 26.

According to various exemplary embodiments, the cap member 26 sealingly engages the cannula member 10. For example, the cap member 26 is appropriately sized so that the longitudinal wall 34 of the cannula member 10 and the pointed end 162 of the trocar member 18 can be received within the inner cavity 194 and sealed therein. For example, the cap member 26 can be secured to the cannula member 10 about the annular base 106 to form a seal therewith. The cannula member 10 may include an externally threaded portion 210 for engaging internal threads 218 of the cap member 26. For example, the externally threaded portion 210 may correspond to an outer portion of the longitudinal wall 34 proximate the adapter portion 90 or to an outer portion of the annular base 106. For example, a second sealing member 226, such as an O-ring, may be further provided about the externally threaded portion 210 to aid in forming a seal.

Alternatively, the trocar member 18 may include a second externally threaded portion having an outer diameter greater than an outer diameter of the first externally threaded portion 170. The second externally threaded portion may engage the internal threads 218 of the cap member 26, and the cap member 26 is appropriately sized to house the whole of the cannula member 10.

Engagement of the cap member 26 with one of the cannula member 10 and the trocar member 18 forms a portable ready-to-use device for providing an auxiliary air passage to the trachea. The cap member 26 covers the pointed end 162 of the elongated member 146 of the trocar member 18 so that the trocar member 18 can be carried without the pointed end 162 presenting a piercing hazard. When the elongated member 146 and at least outer surfaces of the longitudinal wall 34 are sterilized, sealing the elongated member 146 and the longitudinal wall 34 within the inner cavity 194 of the cap member 26 maintains the elongated member 146 and the longitudinal wall 34 in their sterilized states. For example, a distal end 234 of the cap member 26 defines a loop 242 for attachment with an external member. For example, the cap member 26, and in fact the whole device 2 when assembled, can be attached to a key chain via the loop 242 so that it can be conveniently carried without getting lost. When there is a need to urgently use the cannula member 10 and the trocar member 18, the cannula member 10 and the trocar member 18 are disengaged from the cap member 26 so that they can be used to perform a tracheotomy, whereas the cap member 26 conveniently stays on the key chain or the like, and does not get lost.

Disengagement of the cap member 26 from the one of the cannula member 10 and the trocar member 18 exposes the surgical tool formed of the cannula member 10 and trocar member 18. As the secured engagement of the cannula member 10 and the trocar member 18 is maintained when the cap member 26 is disengaged, the surgical tool is ready for use without requiring further assembly.

The present device 2 could also be modified. For instance, the device 2, according to various exemplary embodiments, could take on a curved configuration, wherein the cannula member (and its associated components) would be curved, as known in conventional tracheotomy devices. The trocar member would have a similar configuration so as to be slidable in the cannula member, as would the cap member so that it could be engaged over at least parts of the assembled cannula and trocar members.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the embodiments and non-limiting, and it will be understood by persons skilled in the art that other variants and modifications may be made without departing from the scope of the embodiments as defined in the claims appended hereto.

The invention claimed is:

1. A device for providing an auxiliary air passage to a trachea, the device comprising:
a cannula member having at least one longitudinal wall defining a channel, first and second openings transverse to a longitudinal axis of the channel and a third opening defined on a side of the longitudinal wall; a marking being provided on a proximal section of the cannula member, the marking being adapted to indicate a relative position of the third opening;
a trocar member having a flanged end and an elongated member extending from the flanged end, the elongated member being insertable within the channel, a pointed end of the elongated member projecting through the first opening when the elongated member is inserted in the channel;
a cap member for sealingly engaging at least one of the cannula member and the trocar member and defining an inner cavity, a portion of the cannula member being sealed within the inner cavity when the cap member sealingly engages said at least one of the cannula member and the trocar member.

2. The device of claim 1, wherein the third opening is oriented transversely to an orientation of the first opening.

3. The device of claim 1, wherein an end of the longitudinal wall defines the first opening and a longitudinal portion of the longitudinal wall defines the third opening, the third opening being located proximate the first opening.

4. The device of claim 1, wherein the third opening provides fluid communication between the channel and an outside environment of the cannula member, independently of the first opening.

5. The device of claim 1, wherein the cannula member further comprises an adapter portion having at least one circumferential wall and an annular base defining together an adapter chamber, the longitudinal wall extending longitudinally from an outer surface of the base and the channel being in communication with the adapter chamber via the second opening and an opening in the annular base.

6. The device of claim 5, wherein a diameter of the circumferential wall is substantially greater than a diameter of the longitudinal wall.

7. The device of claim 6, wherein the diameter of the circumferential wall corresponds to a standard diameter of a ventilation port of a respiratory apparatus, the ventilation port being attachable to the adapter portion of the cannula member to provide fluid communication between the respiratory apparatus and at least one of the first opening and the third opening.

8. The device of claim 5, wherein the adapter portion and the longitudinal wall of the cannula are integrally formed.

9. The device of claim 5, wherein the marking is provided on the adapter portion and is located at an angular position about the longitudinal axis corresponding to an angular position of the third opening.

10. The device of claim 5, wherein the cap member is engageable with the cannula member about the annular base to form a seal therewith.

11. The device of claim 10, wherein the cannula member comprises an externally threaded portion for secured engagement with internal threads of the cap member to form the sealing engagement of the cap member with the cannula member.

12. The device of claim 5, wherein the flanged end of the trocar member is securable to the adapter portion of the cannula member to seal the adapter chamber.

13. The device of claim 12, wherein the flanged end of the trocar member and the adapter portion of the cannula member remain secured together when the cap member is disengaged from the cannula member.

14. A device for providing an auxiliary air passage to a trachea, the device comprising:
a cannula member having an adapter portion and at least one longitudinal wall extending longitudinally from an annular base of the adapter portion, the adapter portion having at least one circumferential wall defining with the annular base an adapter chamber, the longitudinal wall defining a channel and an end opening at a distal end thereof, at least one side opening being defined on a side of the cannula member at the distal end, a marking being provided on a proximal section of the cannula member, the marking being adapted to indicate a relative position of the side opening, the channel being in communication with the adapter chamber via an opening in the annular base;

a trocar member having a flanged end and an elongated member extending from the flanged end, the flanged end being sealingly securable with the cannula member to seal the adapter chamber and the elongated member being insertable within the channel, a pointed end of the elongated member projecting through the end opening when the elongated member is inserted in the cannula member;

a cap member for sealingly engaging at least one of the cannula member and the trocar member and defining an inner cavity, a portion of the cannula member being sealed within the inner cavity when the cap member sealingly engages said at least one of the cannula member and the trocar member.

15. The device of claim 14, wherein a diameter of the circumferential wall is substantially greater than a diameter of the longitudinal wall.

16. The device of claim 14, wherein a diameter of the circumferential wall corresponds to a standard diameter of a ventilation port of a respiratory apparatus, the ventilation port being attachable to the adapter portion of the cannula member to provide fluid communication between the respiratory apparatus and the end opening.

17. The device of claim 14, wherein the adapter portion and the longitudinal wall are integrally formed.

18. The device of claim 14, wherein the cap member is engageable with the cannula member about the annular base to form a seal therewith.

19. The device of claim 18, wherein the cannula member comprises an externally threaded portion for secured engagement with internal threads of the cap member to form the sealing engagement of the cap member with the cannula member.

20. The device of claim 14, wherein the flanged end of the trocar member is securable to the adapter portion of the cannula member to seal the adapter chamber.

21. The device of claim 20, wherein the flanged end of the trocar member and the adapter portion of the cannula member remain secured together when the cap member is disengaged from the cannula member.

22. A method for providing an auxiliary air passage in a trachea, the method comprising:
disengaging a cap member from a trocar member and a cannula member to expose a pointed end of the trocar member;
piercing with the trocar member a neck region and a cricothyroid membrane or an anterior wall of the trachea to position a side opening of the cannula member within the trachea;
disengaging the trocar member from the cannula member to expose an opening in the cannula member, which is in fluid communication with the side opening; and using a marking provided on a proximal visible portion of the cannula member so as to selectively orient the side opening.

23. The method of claim 22, wherein, after the piercing step, there is a step of orienting the side opening of the cannula member in a direction to promote air flow into the trachea, typically toward the lungs.

24. The method of claim 22, wherein the cannula member also includes an end opening adapted to be positioned within the trachea.

25. A device for providing an auxiliary air passage to a trachea, the device comprising:
a cannula having opposed distal and proximal openings and a channel therebetween, a third opening being defined on a side of the cannula at a distal end thereof; and
a trocar having an elongated member insertable within the channel, a penetrating end of the elongated member projecting through the distal opening when the elongated member is inserted in the cannula, and being adapted for penetrating a patient and for positioning the distal end of the cannula in a trachea of the patient, and wherein a marking is provided proximally on the cannula, the marking being adapted to indicate a relative position of the side opening; wherein a cap is provided for sealingly engaging at least one of the cannula and the trocar.

26. The device of claim 25, wherein a portion of the cannula is sealed within an inner cavity of the cap when the cap sealingly engages said at least one of the cannula and the trocar.

27. A device for providing an auxiliary air passage to a trachea, the device comprising:
a cannula having distal and proximal openings and a channel therebetween, the cannula having a proximal adapter and a distal side opening in communication with the channel; a marking being provided proximally on the cannula, the marking being adapted to indicate a relative position of the distal side opening;
a trocar having an elongated member insertable within the channel, the elongated member having a penetrating end, the elongated member projecting through the distal opening of the cannula when the elongated member is inserted in the cannula and the cannula is attached to the trocar in an assembled position thereof, the trocar and the cannula being adapted in the assembled position to penetrate a patient such as to position the distal end of the cannula in a trachea of the patient; wherein a cap is provided for sealingly engaging at least one of the cannula and the trocar.

28. The device of claim 27, wherein the adapter of the cannula is adapted to be mounted to a ventilation port of a respiratory apparatus to provide fluid communication between the respiratory apparatus and the distal opening.

29. The device of claim 27, wherein a proximal flanged end of the trocar is sealingly securable with the proximal adapter of the cannula in the assembled position.

30. The device of claim 27, wherein the cap defines an inner cavity, a portion of the cannula being sealed within the inner cavity when the cap sealingly engages said at least one of the cannula and the trocar.

* * * * *